United States Patent [19]

Fleischle

[11] Plant 4,947

[45] Nov. 16, 1982

[54] DISTINCT VARIETY OF STREPTOCARPUS NAMED NICKY

[75] Inventor: Gerhard Fleischle, Vaihingen, Fed. Rep. of Germany

[73] Assignee: Oglevee Associates, Inc., Connellsville, Pa.

[21] Appl. No.: 204,349

[22] Filed: Nov. 5, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its plum-purple flower and its compact habit.

1 Drawing Figure

BACKGROUND OF THE NEW PLANT

The present invention comprises a new and distinct cultivar of *Streptocarpus* × *hybridus* known by the varietal name Nicky. The new cultivar is a mutation achieved through irradiation of Marna, formerly named Neptune Blue (U.S. Pat. No. 4,524).

The new cultivar is most similar to Marna. However, Nicky has a more compact habit, i.e., shorter leaf length, shorter flower stem, more flowers/stem and a more intense petal color than Marna.

The new cultivar was discovered in 1978 in Vaihingen, Federal Republic of Germany; was first asexually reproduced by cuttings in Vaihingen, Federal Republic of Germany; and has been asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of nine weeks from a plantlet (a well rooted young plant in a five centimeter pot) to a flowering plant in a ten centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on nine week plants blossomed under natural light in a greenhouse and color readings were taken indoors under 100 foot candles of cool white fluorescent light. Color references are primarily to the R.H.S. color chart of the Royal Horticultural Society of London. Some color reference is to Exotica III and such reference is duly noted.

Botanical classification: Gesneriaceae (Family); *Streptocarpus*×*hybridus* (Genus×Species).

Flower:

*Fully expanded.*—5.5 centimeters.

*Borne.*—In clusters of one to six flowers per stalk above foliage. Flower stalks arise from mid-rib of each leaf.

*Stems.*—Single, long and pubescent.

*Form.*—Funnel formed in an umbel.

Color:

*Front of petals.*—Fan 2, Violet Blue Group 89-A.

*Throat.*—Fan 1, Yellow-Green Group 1-B with a plurality of stripes Fan 2 Violet Blue Group 89-A extending in center of petals.

*Base of petals.*—Fan 2 Violet-Blue Group 91-B.

*Reverse of petals.*—Fan 2 Violet Group 83-B.

*Tonality from a distance.*—Plum-Purple Exotica III.

*Discoloration.*—Insignificant.

Petals:

*Texture.*—Velvet.

*Appearance.*—Individually lobed and smooth margin.

*Arrangement.*—Regularly united into an elliptical form.

*Fragrance.*—None.

Reproductive organs:

*Anthers.*—Two per flower and interconnected.

*Filament.*—Three fourths of a centimeter initiating from the base of the petal and extending to the anther.

*Pollen.*—Generally nonfertile.

*Style.*—Extends from the tip of the ovary one centimeter and terminates in a flattened stigma.

*Ovaries.*—Long and narrow, one centimeter long and one and one-half millimeters in diameter.

Plant:

*Form.*—Leaves rosulate from a crown at the soil line.

*Growth.*—A spreading, free flowing habit with leaf bases being attenuate.

*Height from soil line.*—10 to 15 centimeters.

*Spread.*—30 to 35 centimeters.

Foliage:

*Size.*—Approximately 18 centimeters in length and 5 to 8 centimeters in width at the widest point.

*Shape.*—Oblanceolate.

*Top side.*—Fan 3 Green Group 137-A.

*Underside.*—Fan 3 Yellow Green Group 146-C.

*Ribs and veins.*—Pinnate.

*Ribs and vein color.*—Fan 3 Green Group 139-D.

*Margin.*—Crenate serrations.

*Stipules.*—None.

I claim:

1. A new and distinct variety of Streptocarpus substantially as herein shown and described.

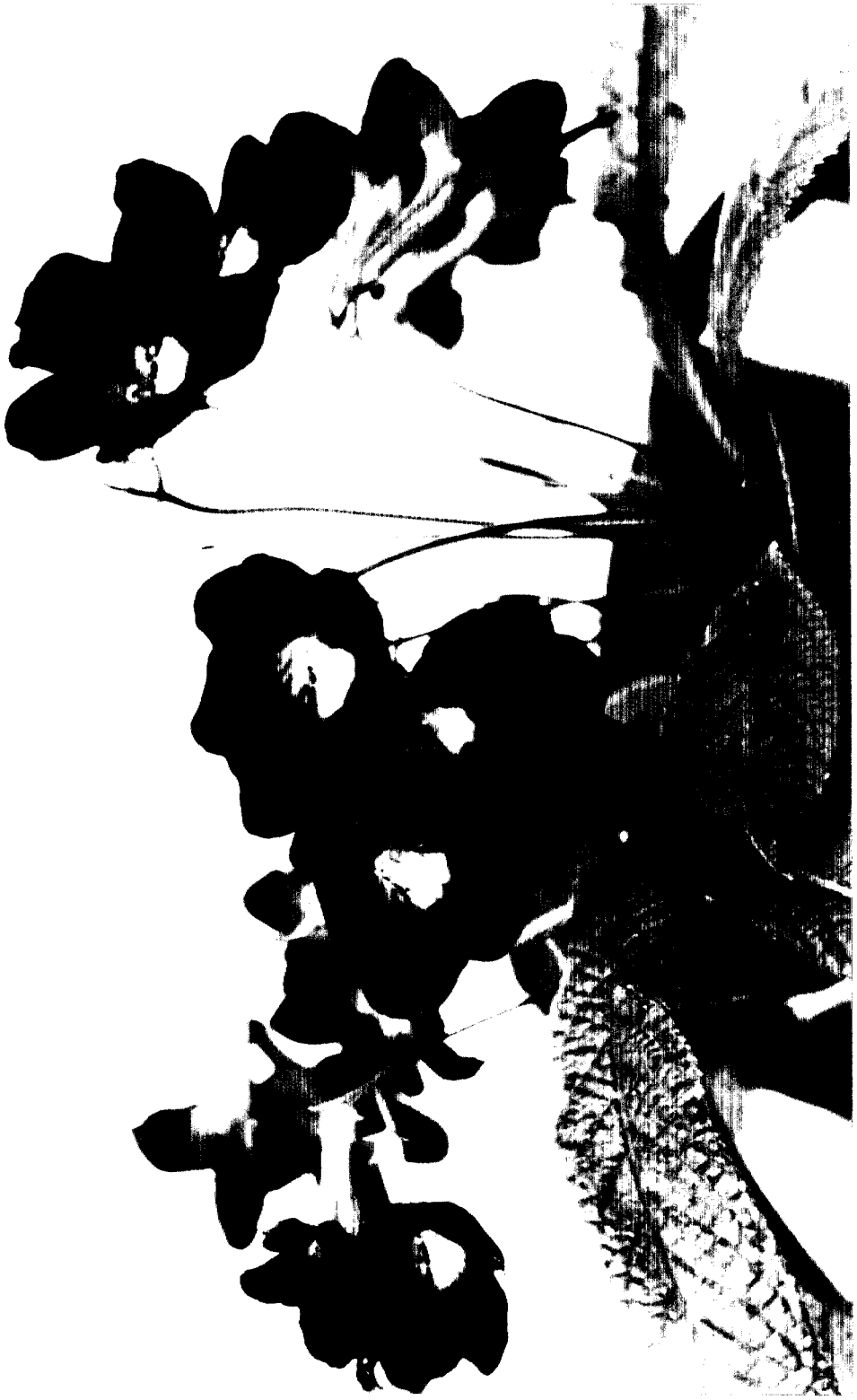

* * * * *